United States Patent
Flosser et al.

(10) Patent No.: US 9,416,092 B2
(45) Date of Patent: Aug. 16, 2016

(54) TRANSESTERIFICATION PROCESS

(71) Applicant: Rohm and Haas Company, Philadelphia, PA (US)

(72) Inventors: David A. Flosser, Missouri City, TX (US); Philippe P. Maillot, Kingwood, TX (US); Nawal K. Sharma, League City, TX (US); Alejandro Ceron, La Porte, TX (US); Mingyu Ye, Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 33 days.

(21) Appl. No.: 14/382,686

(22) PCT Filed: Feb. 11, 2013

(86) PCT No.: PCT/US2013/025527
§ 371 (c)(1),
(2) Date: Sep. 3, 2014

(87) PCT Pub. No.: WO2013/137998
PCT Pub. Date: Sep. 19, 2013

(65) Prior Publication Data
US 2015/0045583 A1 Feb. 12, 2015

Related U.S. Application Data

(60) Provisional application No. 61/611,281, filed on Mar. 15, 2012.

(51) Int. Cl.
*C07C 67/317* (2006.01)
*C07C 67/03* (2006.01)
*C07D 233/32* (2006.01)

(52) U.S. Cl.
CPC ............... *C07C 67/317* (2013.01); *C07C 67/03* (2013.01); *C07D 233/32* (2013.01); *Y02P 20/582* (2015.11)

(58) Field of Classification Search
CPC ...... C07C 67/03; C07C 67/317; C07D 233/32
See application file for complete search history.

(56) References Cited

U.S. PATENT DOCUMENTS

| | | | |
|---|---|---|---|
| 4,202,990 A | | 5/1980 | Murakami et al. |
| 5,072,027 A | * | 12/1991 | Kobayashi .............. C07C 67/03 560/217 |
| 5,504,243 A | * | 4/1996 | Sakamoto ............... C07C 51/50 560/205 |
| 5,610,313 A | | 3/1997 | Riondel et al. |
| 6,008,371 A | | 12/1999 | Knebel et al. |
| 6,509,494 B1 | | 1/2003 | Weir |
| 7,528,278 B2 | | 5/2009 | Benderly et al. |
| 2006/0173191 A1 | | 8/2006 | Curtis |

FOREIGN PATENT DOCUMENTS

EP 453638 10/1991

OTHER PUBLICATIONS

Handbook of Chemistry and Physics, 96th Edition, 2015-2016, pp. 6-210 to 6-213.*

* cited by examiner

*Primary Examiner* — Paul A Zucker
*Assistant Examiner* — Mark Luderer
(74) *Attorney, Agent, or Firm* — Edward L. Brant

(57) ABSTRACT

A transesterification process produces a (meth)acrylate ester product from a mixture comprising an alkyl(meth)acrylate reactant, an alcohol reactant, a catalyst, and a polymerization inhibitor. The mixture is subjected to reaction conditions sufficient to produce a product (meth)acrylate and a product alcohol, which are different than the reactants.

2 Claims, No Drawings

TRANSESTERIFICATION PROCESS

CROSS-REFERENCE TO RELATED APPLICATIONS

This application claims priority from provisional application Ser. No. 61/611,281, filed Mar. 15, 2012, which is incorporated herein by reference in its entirety.

BACKGROUND OF THE INVENTION

The invention relates to a transesterification process for the production of acrylic ester monomers from alkyl (meth)acrylates and alcohols.

The transesterification reaction between alcohols and alkyl (meth)acrylates is known and commercially practiced. As typically conducted in commercial scale processes, the (meth)acrylate reactant and the catalyst are recycled.

U.S. Pat. No. 5,610,313 discloses a process for the preparation of alkyl imidazolidone (meth)acrylates that employs, as a catalyst, a mixture formed of (a) at least one magnesium alkoxide and (b) a component chosen from the chelates of calcium with 1,3-dicarbonyl compounds, dialkyltin oxides, dialkyltin alkoxides and dialkyltin diesters. That patent recommends that maximum dehydration is achieved before addition of the catalyst to the reactants.

U.S. Pat. No. 7,528,278 teaches a transesterification process that involves reacting certain alcohols with an alkyl (meth)acrylate in the presence of a mixed salt catalyst under specified conditions. The mixed salt catalyst can tolerate up to 3,000 ppm water. The patent teaches that prior art catalysts, such as dibutyl tin oxide and lithium hydroxide, are subject to deactivation in the presence of water, and that maximum dehydration of the contents of the reaction vessel should be achieved before addition of said catalysts.

EP-A1-1 686 118 discloses a transesterification process comprising preparing a reaction mixture of alcohol, alkyl (meth)acrylate and polymerization inhibitor, removing water until the water content of the mixture is no more than 1200 ppm, adding at least 2 charges of catalyst, and heating the mixture to commence the reaction.

It would be desirable to have a higher productivity process where all reaction materials could be present in the reaction mixture during dehydration.

SUMMARY OF THE INVENTION

The invention is such a process comprising:
a) forming a mixture by admixing:
a1) reactant alkyl (meth)acrylate;
a2) from 10 to 10,000 parts per million by weight, based on the weight of the alkyl (meth)acrylate charge, of a free radical polymerization inhibitor; and
a3) a reactant alcohol and:
a4) a catalyst;
with the proviso that the molar ratio of reactant alcohol to reactant alkyl (meth)acrylate is from 1:1 to 1:20, and the catalyst is present in a catalytic amount;
b) dehydrating the mixture so that it contains less than 0.2 weight percent water, based on the weight of the mixture;
c) reacting the reactant alcohol with the reactant alkyl (meth)acrylate in a reaction zone at a temperature of from 70 to 125° C. and a pressure of from 100 mm Hg (13.3 kPa) to 900 mm Hg (120.0 kPa);
d) creating a crude product by removing a mixture of alkyl (meth)acrylate and alcohol;
f) optionally adding water to enable recycling of the catalyst;
g) optionally recycling the reactant alkyl (meth)acrylate; and
h) optionally distilling the crude product.

Surprisingly, the cycle time of the reaction is reduced when all reaction materials are present during dehydration. Reduced cycle time permits higher productivity. An additional advantage of the process is that less energy is consumed by the process.

DETAILED DESCRIPTION OF THE INVENTION

The process of the invention produces a (meth)acrylate ester product, and in one embodiment involves a first step of forming a mixture which comprises a alkyl(meth)acrylate reactant, an alcohol reactant, a catalyst, and a polymerization inhibitor. The mixture can be dehydrated and subjected to reaction conditions sufficient to produce a product (meth)acrylate and a product alcohol, which are different than the reactants.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; and the term "(meth)acrylic acid" refers to either acrylic acid or methacrylic acid.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

The alkyl(meth)acrylate reactant advantageously has the following Formula I:

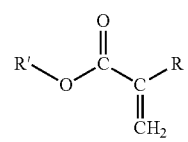

wherein R is H or $CH_3$; and wherein R' is a $C_1$-$C_4$ straight or branched alkyl moiety. In one embodiment of the invention, R and R' are both methyl. Mixtures of alkyl(meth)acrylate reactant can be employed.

Several alcohols are suitable as the reactant alcohol in the process of the invention and include, for example, without limitation: aliphatic linear and branched chain monoalcohols such as, for example, n-butanol, n-propanol, lauryl alcohol, stearyl alcohol, 2-ethylhexanol; cycloaliphatic alcohols, such as cyclohexanol; aromatic alcohols, such as benzyl alcohol; alcohols bearing other functional groups, such as ethylene glycol monomethylether, ethylene glycol monoisopropylether; and alcohols of ethylene oxide adducts of ethylene urea, such as hydroxyethyl ethylene urea (HEEU). Examples of preferred alcohols include HEEU, ethoxylated cetyl stearyl alcohol, such as CSA-20, ethoxylated lauryl myristyl alcohol, dicyclopentenyloxyethyl alcohol, and hydroxyethyl oxazolidine. Advantageously, R'''OH represents the alcohol reactant, where R''' is a substituted or unsubstituted straight chain, branched chain, cyclic, or heterocyclic alkyl moiety, or any combination thereof. For example, R''' may contain heteroatoms such as nitrogen, phosphorous, oxygen, and/or sulfur, and may contain, for example amide, carbonyl, ester, phosphonate, amine, alcohol, and aldehyde functionalities. In addition, R''' may also contain alkenyl or alkynyl functionalities as part of the structure, and may also contain aromatic rings. Mixtures of alcohols can be employed.

The catalyst advantageously is selected from dibutyl tin oxide; reaction products of dibutyl tin oxide with components in the transesterfication of various alcohols with alkyl (meth) acrylates, such as methyl meth(acrylate); dibutyl tin dimethoxide; reaction products of dibutyl tin dimethoxide with components in the transesterification of various alcohols with alkyl (methacrylates); methanolic magnesium methylate; lithium, lithium carbonate, and lithium hydroxide; anhydrous alkali metal hydroxides; hydrates of alkali metal hydroxides; and mixtures thereof. Dibutyl tin oxide is preferred. In one embodiment of the invention, the catalyst is substantially free of chloride and/or fluoride salts. The catalyst is employed in a catalytic amount, i.e. an amount that is at least sufficient to catalyze the reaction of the alcohol with the alkyl(meth)acrylate. The amount of the catalyst added to the reaction vessel advantageously is from 0.1 to 10 mole percent, preferably from 0.5 to 7 mole percent, and more preferably from 1 to 5 mole percent, based on the weight of the alcohol charge.

Suitable polymerization inhibitors include oxygen, diethylhydroxylamine, p-methoxy phenol, hydroquinone, phenothiazine, 2,6-di-t-butylpara-cresol, 3,5-di-t-butyl-4-hydroxyanisole, 2,5-di-t-butylhydroxyanisole, 4-hydroxy-2,2,6,6-tetramethyl piperidinyl free radical (4-hydroxy-TEMPO), 4-methacryloyloxy-2,2,6,6-tetramethyl piperidinyl free radical, and 4-hydroxy-2,2,6,6-tetramethyl N-hydroxy piperidine and mixtures thereof. The total amount of polymerization inhibitor added to the reaction mixture advantageously ranges from lower limits of 10, 100, and 200 to upper limits of 10,000, 5,000, and 3,000 parts per million (ppm) based on the weight of the alkyl(meth)acrylate reactant charge. All ranges used herein are inclusive and combinable. Mixtures of inhibitors can be employed.

Typically, the amount of alkyl(meth)acrylate reactant in the reaction mixture is in stoichiometric excess of the amount of alcohol reactant. For example, the molar ratio of alcohol to alkyl(meth)acrylate advantageously may be from 1:1 to 1:20 or, for example, from 1:2 to 1:6.5, or even from 1:2.2 to 1:3.6. This is because, as discussed in further detail hereinafter, a product alcohol is removed, along with a portion of the alkyl (meth)acrylate reactant, from the reaction mixture by distillation during the period of reaction. In one aspect the product alcohol is removed, along with a portion of the alkyl(meth) acrylate reactant, from the reaction mixture by azeotropic distillation. The removed mixture of reactant alkyl(meth) acrylate and product alcohol may be further separated and the alkyl(meth)acrylate reactant may be recycled to the reaction mixture.

Advantageously, unreacted alkyl(meth)acrylate can be recycled and can contain residual amounts of water such as, for example, from more than 0.2 to 3 weight percent, based on the weight of water and alkyl(meth)acrylate. The process of the invention advantageously involves combining all reaction materials, including the catalyst, during the dehydration step.

The reaction mixture is dehydrated prior to reaction to remove water from the mixture such that the mixture contains less than 0.2 wt. % water. The step of removing water from the reaction mixture may be accomplished, for example, without limitation, by azeotropic distillation of a mixture of water and alkyl(meth)acrylate.

In one aspect of the present invention, only one charge of catalyst is added. The catalyst charge comprises an amount of catalyst equal to from 0.1 to 10 mole %, preferably from 1-2 mol % based on the total moles of alcohol that are present, or which will be present, in the reaction mixture, depending upon which of the foregoing methods of forming the reaction mixture is practiced. The catalyst can be added by any known, conventional delivery means, such as, without limitation, via a pressurized or unpressurized charge hopper, or via a parallel series of individually controlled inline chambers where the catalyst is mixed with the reaction mixture as a carrier, or into a slurry mix with, for example, methyl methacrylate. In one embodiment of the invention, the catalyst is added in multiple charges. In this embodiment, only a portion of the catalyst is present during the dehydration step.

The reaction temperature (i.e., the temperature of the reaction mixture during the transesterification reaction) of the process may be from about 60° C. to 140° C., for example, without limitation, from 70° C. to 125° C., or from 85° C. to 100° C. The reaction pressure may be from 760 mm Hg (atmospheric) (101.3 kPa) to reduced or elevated pressures, such as, for example, from 100 mm Hg (13.3 kPa) to 900 mm Hg (120.0 kPa). As known to those skilled in the art, the reaction temperature can be adjusted as the pressure varies from atmospheric pressure.

As the transesterification reaction proceeds, the products include, but are not necessarily limited to, a product (meth) acrylate and a product alcohol that is different from the reactant alcohol employed to form the reaction mixture. The product (meth)acrylate ester produced by the transesterification process of the present invention advantageously has Formula II as follows:

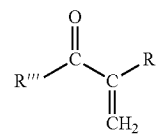

wherein R is H or CH$_3$, and R''' is as described hereinabove. The product alcohol has Formula III as follows:

where R' is as described hereinabove.

For example, when the reactant alcohol is a hydroxyl alkyl imidazolidin-2-one, having the following Formula IV:

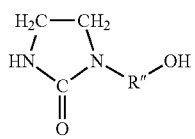

wherein R" is a $C_1$-$C_8$ straight, branched or cyclic, and saturated or unsaturated, hydrocarbon moiety, then the product (meth)acrylate ester has Formula V as follows:

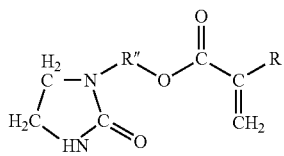

wherein R is H or $CH_3$, and R" is a $C_1$-$C_8$ straight, branched or cyclic, saturated or unsaturated, hydrocarbon moiety.

During the course of the reaction, the product alcohol advantageously is removed from the system, by azeotropic distillation, as an azeotropic mixture of the alkyl(meth)acrylate reactant and the product alcohol.

Particular embodiments of the process of the present invention will now be described in detail in connection with the following examples.

Specific Embodiments of the Invention

The following examples are given to illustrate the invention and should not be construed as limiting its scope. All parts and percentages are by weight unless otherwise indicated.

EXAMPLES

Comparative Experiment 1 (Not an Embodiment of the Invention)

The following experiment demonstrates cycle time under the baseline conditions of doing the dehydration step in the absence of the alcohol.

A mixture of 8.30 grams (0.0333 moles) of dibutyltin oxide catalyst (DBTO), 520 grams (5.09 moles) of methyl methacrylate (MMA), with 2% water added to simulate recycled MMA, and 0.7 grams (0.0040 moles) of 4-hydroxy TEMPO is charged to a 1-liter 4-necked flask equipped with a temperature indicator/controller/magnetic stirrer (Heidolph MR Hei-standard, available from Fisher Scientific, Pittsburgh, Pa. 15275), mixed gas (8% $O_2$-92% $N_2$) sparge inlet, and a 1 inch diameter-15 plate Oldershaw column fitted with a magnetically controlled distillation head, controlled by a repeat cycle timer (ACE Glass 6671-14 continuous 1 to 6000 seconds, available from ACE Glass, Vineland, N.J. 08362), and a graduated distillate receiver. During dehydration of the batch, the mixture is stirred, sparged with mixed gas at a rate of 1 ml/min and heated to reflux at atmospheric pressure, while removing the MMA-water azeotrope. The overhead splitter is set to send 75% of the distillate forward and 25% back to the column. The maximum temperature atop the column is 99.° C. and the maximum temperature in the flask is 105° C. The mixture is dehydrated to a water concentration of <0.10%. Distillation is stopped by turning off the overhead splitter so that no distillate is sent forward, and to the reaction mixture is added 220 grams (1.69 moles) of HEEU. Within 15 minutes of adding HEEU, the overhead temperature equilibrates to about 68-70° C. and the distillation is resumed by turning on the overhead splitter and sending 25% of the distillate forward and 75% back to the column During the subsequent reaction step, the mixture is stirred, sparged with mixed gas, and is continuously heated to reflux at atmospheric pressure while removing the MMA-methanol of reaction azeotrope. The reaction is considered complete when the HEEU concentration is less than 3.0%, at which point the distillation is halted by turning off the overhead splitter so that no distillate is sent forward.

A final product formulation is then prepared by performing a water transfer of the excess methyl methacrylate, as follows. The mixture is cooled to 60-70° C. and about 300 grams of water is added. The flask contents are heated under a reduced pressure of 150 mm Hg, the overhead splitter is turned on to send 75% of the distillate forward and 25% back to the column, and the MMA-water azeotrope is removed. During the removal of excess MMA the contents are stirred and sparged. The catalyst is filtered from the reaction mixture. The procedure is repeated 3 times. The filtered product mixture is a clear yellow liquid. According to quantitative high-performance liquid chromatography (HPLC), the mixtures from the 3 runs contain 50-52 weight % MEEU, 1-3.5 weight % HEEU, and 0.7-0.8 weight % N-(2-methacryloyloxyethyl)-N'-(methacryloyl)ethylene urea (MEMEU) and 0.2-0.8 weight % of MMA. By Karl Fischer analysis the product contained 40-48 weight % water. In all cases the weight percentages total 100% for the product mixture.

The 3 runs have the following cycle times:

|  | Experiment 1 | Experiment 2 | Experiment 3 | Average |
| --- | --- | --- | --- | --- |
| Dehydration (min) | 52 | 45 | 65 | 54 |
| Reaction (min) | 255 | 255 | 250 | 253 |
| Water Transfer (min) | 165 | 160 | 190 | 172 |
| Total (min) | 578 | 591 | 615 | 595 |

Dehydration, reaction, and water transfer times are defined by the actual start (first drop) and stop (last drop) of distillation during those steps. Total time is defined as the time elapsed from the initial application of heat prior to dehydration to the time heat is removed at the end of water transfer.

Example 2

This example demonstrates cycle time reduction under the conditions of combining all materials prior to the dehydration step.

Using the equipment of Comparative Experiment 1, a mixture of 8.30 grams (0.0333 moles) of DBTO, 520 grams (5.09 moles) of MMA, with 2% water added to simulate recycled MMA, 0.7 grams (0.0040 moles) of 4-hydroxy TEMPO, and 226.0 grams (1.74 moles) of HEEU is charged to the flask. During dehydration of the batch, the mixture is stirred, sparged with mixed gas at a rate of 1 ml/min and heated to reflux at atmospheric pressure, while removing the MMA-water azeotrope. The overhead splitter is set to send 75% of the distillate forward and 25% back to the column. The maximum temperature atop the column is 99° C. and the maximum temperature in the flask is 105° C. The mixture is dehydrated to a water concentration of 0.10%. Distillation is stopped by turning off the overhead splitter so that no distillate is sent forward. Within 15 minutes, the overhead temperature equilibrates to about 68-70° C., and the distillation is resumed by turning on the overhead splitter and sending 25% of the distillate forward and 75% back to the column During the subsequent reaction step, the mixture is stirred, sparged with mixed gas, and continuously heated to reflux at atmospheric pressure while removing the MMA-methanol of reaction azeotrope. The reaction is considered complete when the HEEU concentration is less than 3.5%, at which point the distillation is halted by turning off the overhead splitter so that no distillate is sent forward.

A final product formulation is then prepared by performing a water transfer of the excess MMA, as follows. The mixture is cooled to 60-70° C. and about 300 grams of water is added. The flask contents are heated under a reduced pressure of 150 mm Hg, the overhead splitter is turned on to send 75% of the distillate forward and 25% back to the column, and the MMA-water azeotrope is removed. During the removal of excess MMA the contents are stirred and sparged. The catalyst is removed via filtration. The procedure is repeated 3 times. The filtered product mixture is a clear yellow liquid. According to quantitative HPLC, the mixtures from the 3 runs contain 50-53 weight % MEEU, 1-3.5 weight % HEEU, and 0.8-1.16 weight % MEMEU and 0.3-0.9 weight % of MMA. By Karl Fischer analysis the product contains 40-48 weight % water.

The 3 runs have the following cycle times.

|  | Experiment 1 | Experiment 2 | Experiment 3 | Average |
|---|---|---|---|---|
| Dehydration (min) | 75 | 70 | 75 | 73 |
| Reaction (min) | 270 | 255 | 255 | 260 |
| Water Transfer (min) | 90 | 90 | 75 | 85 |
| Total (min) | 490 | 498 | 510 | 499 |

Reaction time, water transfer, and total time are defined hereinabove.

A significant cycle time reduction is achieved when combining all materials prior to dehydration. The average cycle time when HEEU is kept separate from the catalyst during the dehydration step is 595 minutes, while the average cycle time when all materials are combined prior to dehydration is 499 minutes. This unexpectedly equates to a 16% reduction in cycle time. Surprisingly, a significant portion of the cycle time reduction is due to shorter water transfer time.

As demonstrated by Example 2, all materials can be combined in the presence of as much as 2% water prior to dehydration. Surprisingly, the reaction is even more productive when the dehydration is done in the presence of all reaction materials.

What is claimed is:

1. A process comprising:
   a) forming a reaction mixture by admixing methyl methacrylate, a free radical polymerization inhibitor, hydroxyethyl ethylene urea and a catalyst comprising dibutylin oxide catalyst, wherein the reaction mixture further comprises at least 0.2 wt. % water, based on the weight of the reaction mixture;
   b) dehydrating the reaction mixture so that it contains less than 0.2 weight percent water, based on the weight of the reaction mixture;
   c) reacting the hydroxyethyl ethylene urea with the methyl methacrylate in a reaction zone at a temperature of from 70 to 125° C. and a pressure of from 100 mm Hg (13.3 kPa) to 900 mm Hg (120.0 kPa) to produce methacryloxyethyl ethylene urea and methanol;
   d) creating a crude product by removing a mixture of methyl methacrylate and methanol;
   e) optionally adding water to enable recycling of the catalyst;
   f) optionally recycling the methyl methacrylate; and
   g) optionally distilling the crude product.

2. The process of claim 1 wherein the removal of step d) is conducted by azeotropic distillation.

* * * * *